United States Patent [19]

Fike

[11] Patent Number: 5,612,382

[45] Date of Patent: Mar. 18, 1997

[54] COMPOSITION FOR PERCUTANEOUS ABSORPTION OF PHARMACEUTICALLY ACTIVE INGREDIENTS

[75] Inventor: Elmer A. Fike, Nitro, W. Va.

[73] Assignee: Frances B. Fike, Nitro, W. Va.

[21] Appl. No.: 275,423

[22] Filed: Jul. 15, 1994

[51] Int. Cl.$^6$ ............................. A01N 37/18; A01K 31/16
[52] U.S. Cl. ........................ 514/14; 514/629; 514/625; 514/356; 514/570; 514/576; 514/15; 514/227.8; 514/947
[58] Field of Search ................................. 514/629, 947, 514/625, 356, 570, 576, 14, 15, 227.8

[56] References Cited

U.S. PATENT DOCUMENTS

| | | |
|---|---|---|
| 2,431,558 | 11/1947 | Huber . |
| 3,742,951 | 7/1973 | Zaffaroni . |
| 3,797,494 | 3/1974 | Zaffaroni . |
| 3,996,934 | 12/1976 | Zaffaroni . |
| 4,014,334 | 3/1977 | Theeuwes et al. . |
| 4,573,996 | 3/1986 | Kwiatek et al. . |
| 4,913,905 | 4/1990 | Fankhauser et al. . |
| 5,032,403 | 7/1991 | Sinnreich . |
| 5,128,124 | 7/1992 | Fankhauser et al. . |
| 5,128,376 | 7/1992 | Saito et al. . |
| 5,391,548 | 2/1995 | Francouer et al. ................... 514/947 X |
| 5,413,794 | 5/1995 | Suzuki et al. ........................ 514/947 X |
| 5,422,118 | 6/1995 | Brown et al. ........................ 514/947 X |

FOREIGN PATENT DOCUMENTS 60-228423  11/1985  Japan .

OTHER PUBLICATIONS

"Topical minioxidil in early male pattern baldness", Clinical and laboratory studies, Elise A. Olsen et al., Mar. 18, 1985, pp. 185–192.
"Percutaneous Absorption of Minioxidil in Man", T. Franz, M. D., Arch Dermatol — vol. 121, Feb. 1985, pp. 203–206.
"Rogaine" Data sheets (Four Sheets), 1992.
Excerpt of "Transderm Scop" Transdermal Therapeutic System, Distributed by CIBA Consumer Pharmaceutical (Rev. Feb. 1988) 2 pages.
Merck Index, 11th Edition, 1989, p. 976.

*Primary Examiner*—Paul F. Shaver
*Attorney, Agent, or Firm*—Oliff & Berridge

[57] ABSTRACT

A pharmaceutical composition for transdermally delivering pharmaceutically active ingredients through skin or mucosal tissues. The composition comprises pharmaceutically active ingredients in admixture with a pharmaceutically acceptable carrier that is a hydroxy alkyl amide. The composition exhibits an improved ability to control the rate of delivery of the pharmaceutically active ingredients into the body.

24 Claims, No Drawings

COMPOSITION FOR PERCUTANEOUS ABSORPTION OF PHARMACEUTICALLY ACTIVE INGREDIENTS

FIELD OF THE INVENTION

The present invention relates to a composition containing pharmaceutically active ingredients that exhibits superior percutaneous absorption properties. The invention also relates to a method of treating ailments by the transdermal administration of such composition.

BACKGROUND

Administration of pharmaceutically active ingredients to the skin or mucosal tissues is known, both to treat local symptoms and to treat systemic disorders. Such dermal application is a desirable alternative to oral administration because, especially with regard to local symptoms, dermal application allows higher doses of the active ingredients to be administered in the location they are most needed. The same high dose level often cannot be given orally due to the digestive system becoming upset from the high level of active ingredient, and because of toxicity problems with higher oral doses for most active ingredients. Thus, oral administration may require low doses and can be less effective than direct transdermal administration.

A difficulty with transdermal administration is that normal skin is relatively impermeable to most pharmaceutically active ingredients. Thus, it is often necessary to use pharmaceutically acceptable carriers to enhance the percutaneous absorption of the active ingredient.

An additional problem related to transdermal administration of active ingredients is that the pharmaceutically acceptable carrier may result in such rapid absorption of the active ingredient in the body of the patient that the active ingredient is too rapidly dissipated within the body to be effective over any period of time. Thus, repeated applications are necessary. Alternatively, the use of bulky and uncomfortable patches may be necessary in order to provide prolonged dermal exposure to the composition containing the active ingredients.

U.S. Pat. No. 2,431,558 (Huber) discloses the use of esters of nicotinic acid as vasodilators. The nicotinic acid esters may be applied to the skin of humans or animals as a composition in solution with mineral, vegetable or animal oils or greases, or emulsions thereof.

U.S. Pat. No. 5,128,376 (Saito et al.) relates to the percutaneous administration of a physiological active agent in a carrier system comprising at least one adjuvant, at least one solvent and at least one diol and/or triol moderator. The large list of possible suitable solvents at col. 4, line 37 to col. 5, line 35 includes amide solvents. The reference does not disclose the use of hydroxy alkyl amides.

Japanese Patent Application 60-228,423 (Tamura et al.) discloses a carrier composition for external drug application comprising azulene, camazulene or guaiazulene and a specific polar compound that exhibits improved permeation and absorption of drugs into the skin. Among the many suitable polar compounds are listed amide compounds. There is no disclosure of the use of the amide compounds without one of the azulene compounds, nor is there any suggestion that hydroxy alkyl amides are a superior carrier of drugs.

U.S. Pat. Nos. 3,742,951, 3,797,494, and 3,996,934 (all to Zaffaroni) relate to controlled administration of active drugs by the use of bandages having reservoirs containing the drug and wall members for controlling the rate of drug release to the skin. The drug can be used alone in the reservoir or in combination with a carrier or a transport agent. The transport agents are disclosed to aid or assist the drug delivery device to achieve the administration of a drug to a drug receptor. The broad list of transport agents include N,N-di(lower) alkylacetamides including N-(2-hydroxyethyl) acetamide, but there is no teaching or suggestion of the superiority of such transport agents over other carriers or transport agents.

U.S. Pat. No. 4,014,334 (Theeuwes et al.) discloses a laminated osmotic dispensing system for delivery of a beneficial agent. The system is preferably oral, but dermal application is also disclosed. The beneficial agent in the dispensing system may be in the form of a solution, but there is no disclosure of any suitable solvents or carriers.

U.S. Pat. No. 4,573,996 (Kwiatek) relates to a device for administration of an active agent to a host by transdermal means. The active agent may be present either alone or in combination with other active agents and/or a pharmaceutically acceptable carrier or transporting agent. The list of transporting agents includes N,N-di(lower alkyl) acetamides and N-(2-hydroxyethyl) acetamide.

U.S. Pat. Nos. 4,913,905 and 5,128,124 (both to Fankhauser et al.) relate to a transdermal delivery system for administration of oestrogens and gestagens. The active agent in the reservoir of the system is used in combination with a penetration enhancer. N-2-hydroxyethyl acetamide is disclosed as a penetration enhancer, but alkanols are preferred. No benefits from the use of N-2-hydroxyethyl acetamide are disclosed or suggested.

U.S. Pat. No. 5,032,403 (Sinnreich) discloses a multilayer transdermal therapeutic system for the administration of active substances. The reservoir contains the active agent along with a penetrating agent that may be N,N-di-loweralkylacetamide or N-2-hydroxyethyl acetamide, among others. No benefit from the use of N-2-hydroxyethyl acetamide is disclosed or suggested.

None of the above references discloses or suggests any benefit from the use of hydroxy alkyl amides as a carrier material for a pharmaceutically active agent to be transdermally administered. The references merely equate all of the large number of known carrier materials with each other in terms of effectiveness.

SUMMARY OF THE INVENTION

The present invention provides improved pharmaceutical compositions for use in topical applications of active ingredients to the skin or mucosal tissues. The invention provides a pharmaceutical composition comprising at least one pharmaceutically active ingredient in admixture with a pharmaceutically acceptable carrier that is a hydroxy alkyl amide. The pharmaceutical composition of the present invention exhibits an improved capability of treating and alleviating symptoms associated with ailments in localized portions of the body. The present invention thus provides a transdermal pharmaceutical composition with advantages neither disclosed nor recognized in the prior art.

The present invention also provides a method of treating localized symptoms of specific ailments such as carpal tunnel syndrome, split finger syndrome, etc. by topically applying a pharmaceutical composition comprising active ingredients effective to treat such symptoms in admixture with a pharmaceutically acceptable carrier comprising a hydroxy alkyl amide.

DETAILED DESCRIPTION OF PREFERRED EMBODIMENTS

The composition of the present invention for transdermally delivering active ingredients into the body comprises at least one pharmaceutically active ingredient in admixture with a pharmaceutically acceptable carrier that comprises at least one hydroxy alkyl amide. The at least one pharmaceutically active ingredient is preferably present in amounts effective to alleviate or provide relief from symptoms of an ailment sought to be treated by the composition. More than one active ingredient may be present in the composition. Preferably, the overall weight percentage of the active ingredient is 0.1 to 25 wt. % of the weight of the composition and active ingredient.

The pharmaceutically acceptable carrier comprises at least one hydroxy alkyl amide. The carrier may be a mixture of more than one hydroxy alkyl amide. By hydroxy alkyl amide is meant compounds of the following formula:

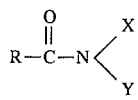

wherein R=an alkyl or acyl group of 1 to 10 carbon atoms, X=H, OH or alkyl groups of 1 to 10 carbon atoms in length which may or may not contain an hydroxy group, and Y=H, OH or alkyl groups of 1 to 10 carbon atoms in length which may or may not contain an hydroxy group, wherein at least one of X and Y must contain at least one hydroxy group. The hydroxy groups can be located in the terminal position of the chain, or they can be located at any position in the chain.

Examples of hydroxy alkyl amide compounds include, but are not limited to, N-(2-hydroxyethyl) acetamide, dihydroxyethyl acetamide, N-acetyl propanolamine, N-acetyl dipropanolamine, N-acetyl isopropanolamine and N-acetyl diisopropanolamine. Preferably, the pharmaceutically acceptable carrier is N-(2-hydroxyethyl) acetamide.

Methods of preparing hydroxy alkyl amides in general are known. Hydroxy alkyl amides have utility not only as pharmaceutically acceptable carriers for transdermal compositions, but are also known to be used as solvents due to the presence of both an amide and a hydroxyl group. Other known uses of hydroxy alkyl amides include use in cosmetic preparations and as hair conditioning agents. N-(2-hydroxyethyl) acetamide has approval from the United States Food and Drug Administration as a material safe for use upon human skin. Because of the similar chemical structure of compounds comprising the hydroxy alkyl amide class, it is believed that all hydroxy alkyl amides are safe when used in contact with human skin. Further, all hydroxy alkyl amides would be expected to show the same advantages with respect to delivering a pharmaceutical active ingredient through human tissue to the area in the body requiring treatment with the pharmaceutically active ingredient.

Without wishing to be bound by any theory, it is believed that the improved results achievable by the present composition in treating or alleviating symptoms associated with ailments in localized areas are due to the ability of the hydroxy alkyl amide carriers to carry pharmaceutically active ingredients through the skin or mucosal tissues in a controlled manner. In other words, the hydroxy alkyl amide carriers do not penetrate the skin or mucosal tissues at such a rapid rate that the pharmaceutically active ingredients are quickly dissipated within the body cavity. Rather, it is believed that the hydroxy alkyl amides have such a penetration rate that the pharmaceutically active ingredients are transported to the localized area requiring treatment over a period of time sufficient to allow maximum use of the pharmaceutically active ingredient in treating the localized symptoms. Loss of pharmaceutically active ingredients is usually due to dissipation within the body cavity because absorption is too rapid and/or due to external loss when the composition is rubbed off prior to having an opportunity to penetrate the skin because absorption is too slow. Hydroxy alkyl amides minimize both types of losses as hydroxy alkyl amides have a penetration rate through the skin or mucosal tissues of humans that is ideally suited for sustained delivery of pharmaceutically active ingredients.

The pharmaceutically active ingredients that can be used in admixture with the hydroxy alkyl amide carriers are not limited. Examples of pharmaceutically active ingredients include antimicrobial agents such as penicillin, tetracycline, bacitracin, sulfonamides and Neosporin® (a proprietary mixture of polymyxin B sulfate, bacitracin zinc and neomycin), vasodilators such as niacin or nicotinic acid (derivatives of vitamin $B_3$), nifedipine, nitroglycerin and other compounds having a nitrate moiety such as amyl nitrate, sodium nitrate and pentaerythritol tetranitrate; muscle relaxants such as mephenesin, methocarbomal, trihexylphenidyl and biperiden; muscle contractants such as atropine, scopolamine, methscopolamine, oxyphenonium and papaverine; analgesics such as morphine, codeine, meperidine and nalorphine; anti-inflammatory agents such as aspirin, methyl salicylate, salicylamide and ibuprofen; anesthetics such as procaine, lidocaine, naepaine, piperocaine and dibucaine; hormones such as cortisone; androgenic steroids such as methyl testosterone and fluoxmesterone; estrogenic steroids such as estrone and estradiol; progestational steroids such as progesterone; and nutritional agents such as vitamins, essential amino acids and essential fats. In addition, the hydroxy alkyl amides may be used as a carrier with minoxidil (2,4-pyrimidinediamine, 6-(1-biperidinyl)-3-oxide) and glycosamine.

As the pharmaceutically active ingredients are not limited, the selection of pharmaceutically active ingredients is dependent upon the symptoms associated with the ailment that is sought to be treated.

For the treatment of localized pain, the pharmaceutically active ingredient may be ibuprofen or aspirin. For symptoms of ailments that may be treated by increasing the circulation of blood in the localized area, the composition preferably includes vasodilators such as vitamin $B_3$ or derivatives thereof such as niacin and nicotinic acid. Compositions using niacin, for example, may also be used as skin conditioners to soften, moisturize and reduce the flakiness of skin. Compositions comprising niacin and an analgesic such as ibuprofen or aspirin may be used to alleviate sunburn pain and promote healing as well as to condition the skin. For exposed wounds, it is preferable to include in the composition antimicrobial agents such as bacitracin or Neosporin® in an amount of from 0.01 to 5, more preferably 0.01 to 2.0, percent by weight of the composition.

For specific ailments such as arthritis, the composition should comprise vitamin $B_3$ or its derivatives in an amount of from 0.1 to 15 percent by weight of the composition as the pharmaceutically active ingredients, along with the inclusion in the composition of analgesics or anti-inflammatory agents in an amount of 0.1 to 15 percent by weight of the composition.

Split finger syndrome or hemorrhoidal tissues may be treated with a composition containing nicotinic acid or other forms of vitamin $B_3$ in an amount from 0.1 to 15 percent by weight of the composition as the pharmaceutically active ingredient. To further promote healing, 0.01 to 5, more preferably 0.01 to 2.0, percent by weight of an antimicrobial agent can be added to the composition.

Carpal tunnel syndrome may be treated with a composition containing vitamin $B_6$ as the pharmaceutically active ingredient in an amount of 0.1 to 15 percent by weight of the composition. Such composition also preferably includes vitamin $B_3$ or its derivatives in an amount of 0.1 to 15 percent by weight and an analgesic or anti-inflammatory agent in an amount of 0.1 to 15 percent by weight to alleviate symptoms related to carpal tunnel syndrome.

An advantage of transdermal applications of pharmaceutically active ingredients over oral application of the same ingredients is that increased dosages of the active ingredient can be utilized in the localized area requiring treatment. Also, the use of hydroxy alkyl amides as the carrier in a pharmaceutical composition eliminates the need for controlled release delivery devices such as bandages and plasters that are known in the art, for example such as in U.S. Pat. No. 4,573,996 to Kwiatek et al., as the carrier is alone effective to meter the rate of carrying the pharmaceutically active ingredient into the body. However, the presently disclosed pharmaceutical composition may be included in such controlled release structures if so desired, although physical application to the skin is preferred.

Because different symptoms of different ailments require different dosage levels, the amount of daily applications of the transdermal pharmaceutical composition varies depending on the ailment. Generally, the composition should be applied to the skin of the localized area requiring treatment about 1 to 5 times per day. Each application should be approximately 0.1 to 2 cc of the composition. The pharmaceutical active ingredients can, for example, be applied in amounts of 10 to 500 milligrams per day. The amount of pharmaceutical active ingredient in the composition may be increased or decreased depending on if it is desirable to have greater or fewer applications daily, respectively. Each active ingredient should be present in the composition in an amount ranging from 0.01 to 20 weight percent based on the weight of the composition and the active ingredient, preferably 0.1 to 15 weight percent, most preferably 2 to 7 weight percent. The total amount of active ingredients present in the composition preferably does not exceed 25 wt. %, based on the weight of the composition.

EXAMPLES

The following examples are intended to illustrate embodiments of the invention.

Example 1

A pharmaceutical composition is made by admixing niacin in an amount of 5% by weight of the composition in N-2-hydroxyethyl acetamide. The composition is topically applied to affected regions of the skin of a patient suffering from split finger syndrome, an ailment characterized by dryness and splitting of the skin. The composition is applied two to five times daily in an amount of a few drops (1 drop is approximately 0.1 to 0.5 cc) on the affected area. Within as little as three days, the outward symptoms of split finger syndrome showed signs of healing. After application of about 1,000 mg of the composition (50 mg of niacin) over a 10 day period, the symptoms were substantially eliminated.

Example 2

The composition of Example 1, applied in amounts similar to those in Example 1, also improves healing of skin wounds, including diabetic ulcers, and skin bruises. For a patient suffering from easy bruising, with bruises that take two to three weeks to heal, the bruises are healed in two to four days following application of the pharmaceutical composition.

Example 3

The symptoms of carpal tunnel syndrome include pain and burning or tingling in the fingers and hand, sometimes extending to the elbow. A pharmaceutical composition to treat the symptoms of carpal tunnel syndrome is prepared, and comprises, in admixture, 5% by weight niacin, 5% by weight ibuprofen, 5% by weight pyridoxine (vitamin $B_6$) and 85% by weight N-2-hydroxyethyl acetamide. The pharmaceutical composition is applied to the forearm and hands of a patient suffering from carpal tunnel syndrome two to five times a day using a few drops per application. Within two days to a week, the symptoms of carpal tunnel syndrome show significant alleviation in that the patient is able to move his wrist and fingers free of pain.

Example 4

Arthritis is characterized by inflammation of the joints causing pain and loss of movement in the joint. A composition comprising 5% by weight niacin as a vasodilator, 5% by weight ibuprofen as an anti-inflammatory agent and 90% by weight N-2-hydroxy ethyl acetamide as a carrier is prepared. The composition is topically applied from two to four times a day to the skin surrounding joints of a patient suffering from arthritis. Each application comprises a few drops (less than 1 cc total). Within about one day to five days, the pain associated with arthritis is substantially alleviated and the swelling significantly reduced.

Example 5

A pharmaceutical composition for treating cuts and other wounds of the skin is prepared and comprises 5% by weight niacin, 0.1% by weight bacitracin as an antimicrobial agent and 94.9% by weight N-2-hydroxyethyl acetamide as a carrier. The topical application of the composition directly to wounds, in an amount varying from 10 to 100 mg per day of the composition, speeds the normal healing process of the wounds. With the application of the composition, such wounds heal in 2 to 4 days, compared to 3 to 7 days healing time without application of any healing material.

Example 6

Raynaud's disease is caused by a deficiency of blood due to functional constriction or obstruction of a blood vessel in the hands and feet, and is accompanied by numbness and pain. A composition comprising 3% by weight nifedipine and 97% by weight N-2-hydroxyethyl acetamide applied topically to the feet of a Raynaud's disease sufferer eliminates the numbness within minutes as well as eliminating the feeling of coldness. The composition shows these healing abilities after only one application of less than 1 cc.

Example 7

Another composition for treating arthritis symptoms is made by mixing 10% by weight of the composition methyl salicylate with 90% by weight N-2-hydroxyethyl acetamide. Four applications (approximately 0.1–2 cc per application) over a one hour period relieves the patient of shoulder and back arthritic pain. Adding 5% by weight niacin to the composition additionally relieves stronger arthritic pain experienced in the neck of the patient when applied four times over a two hour period.

While this invention has been described in conjunction with specific embodiments thereof, it is evident that many alternatives, modifications, and variations will be apparent to those skilled in the art. Accordingly, it is intended to embrace all such alternatives, modifications and variations as fall within the spirit and scope of the appended claims.

What is claimed is:

1. A pharmaceutical composition for transdermal application, comprising at least one pharmaceutically active ingredient, present in an amount effective to treat symptoms of a local disease or ailment, in admixture with a pharmaceutically acceptable carrier capable of penetrating skin or mucosal tissue, said pharmaceutically acceptable carrier consisting essentially of at least one hydroxy alkyl amide selected from the group consisting of N-(2-hydroxyethyl) acetamide, dihydroxyethyl acetamide, N-acetyl propanolamine, N-acetyl dipropanolamine, N-acetyl isopropanolamine and N-acetyl diisopropanolamine.

2. A pharmaceutical composition according to claim 1, wherein said pharmaceutically active ingredient is present in an amount of 0.01 to 25 wt. % of said composition.

3. A pharmaceutical composition according to claim 1, wherein said at least one hydroxy alkyl amide is N-(2-hydroxyethyl) acetamide.

4. A pharmaceutical composition according to claim 1, wherein said pharmaceutically active ingredient is selected from the group consisting of vasodilators, antimicrobial agents, analgesics, anti-inflammatory agents, anesthetics, muscle relaxants, muscle contractants, hormones, steroids and nutritional agents.

5. A pharmaceutical composition according to claim 1, wherein said at least one pharmaceutically active ingredient is selected from the group consisting of ibuprofen, aspirin and methyl salicylate.

6. A pharmaceutical composition according to claim 1, wherein said at least one pharmaceutically active ingredient comprises 0.1 to 15 wt. % of a vasodilator and 0 to 15 wt. % of an analgesic or anti-inflammatory agent, based on the weight of the composition.

7. A pharmaceutical composition according to claim 6, wherein said vasodilator is niacin.

8. A pharmaceutical composition according to claim 1, wherein said at least one pharmaceutically active ingredient comprises 0.01 to 5 wt. % of an antimicrobial agent and 0 to 15 wt. % of an analgesic or anti-inflammatory agent, based on the weight of the composition.

9. A pharmaceutical composition according to claim 1, wherein said at least one pharmaceutically active ingredient comprises 0.1 to 5 wt. % of minoxidil based on the weight of the composition.

10. A pharmaceutical composition for transdermal application, comprising at least one pharmaceutically active ingredient selected from the group consisting of vasodilators, antimicrobial agents, analgesics and anti-inflammatory agents, present in an amount effect to treat symptoms of a local disease or ailment, in admixture with a pharmaceutically acceptable carrier capable of penetrating skin or mucosal tissue, said pharmaceutically acceptable carrier consisting essentially of at least one hydroxy alkyl amide selected from the group consisting of N-(2-hydroxyethyl) acetamide, dihydroxyethyl acetamide, N-acetyl propanolamine, N-acetyl dipropanolamine, N-acetyl isopropanolamine and N-acetyl diisopropanolamine.

11. A pharmaceutical composition for transdermal application, comprising at least one pharmaceutically active ingredient selected from the group consisting of niacin, ibuprofen, aspirin, methyl salicylate, salicylamide, vitamin $B_6$, nifedipine and bacitracin, present in a amount effective to treat symptoms of a local disease or ailment, in admixture with a pharmaceutically acceptable carrier capable of penetrating skin or mucosal tissue, said pharmaceutically acceptable carrier consisting essentially of at least one hydroxy alkyl amide selected from the group consisting of N-(2-hydroxyethyl) acetamide, dihydroxyethyl acetamide, N-acetyl propanolamine, N-acetyl dipropanolamine, N-acetyl isopropanolamine and N-acetyl diisopropanolamine.

12. A method of treating a subject suffering from symptoms of a disease or ailment in a localized area, comprising topically applying to said localized area a composition comprising an amount of a pharmaceutically active ingredient effective to alleviate or eliminate said symptom and, in admixture with said pharmaceutically active ingredient, at least one hydroxy alkyl amide carrier selected from the group consisting of N-(2-hydroxyethyl) acetamide, dihydroxyethyl acetamide, N-acetyl propanolamine, N-acetyl dipropanolamine, N-acetyl isopropanolamine and N-acetyl diisopropanolamine.

13. A method according to claim 12 wherein said composition is topically applied without the use of any delivery device.

14. A method according to claim 12, wherein said disease or ailment is arthritis.

15. A method according to claim 14, wherein said pharmaceutically active ingredient comprises 0.1 to 15 wt. % of a vasodilator and 0.1 to 15 wt. % of an analgesic or anti-inflammatory agent.

16. A method according to claim 15, wherein said vasodilator is niacin and said anti-inflammatory agent is ibuprofen.

17. A method according to claim 12, wherein said disease or ailment is carpal tunnel syndrome.

18. A method according to claim 17, wherein said pharmaceutically active ingredient comprises 0.1 to 15 wt. % of a vasodilator, 0.1 to 15 wt. % of an analgesic or anti-inflammatory agent and 0.1 to 15 wt. % of vitamin $B_6$.

19. A method according to claim 18, wherein said vasodilator is niacin and said anti-inflammatory agent is ibuprofen.

20. A method according to claim 12, wherein said ailment is a skin wound.

21. A method according to claim 20, wherein said pharmaceutically active ingredient comprises 0.1 to 15 wt. % of a vasodilator and 0.01 to 5 wt. % of an antimicrobial agent.

22. A method according to claim 21, wherein said antimicrobial agent is bacitracin.

23. A method of conditioning skin, comprising topically applying to said skin a composition comprising an amount of niacin effective to condition said skin, and, in admixture with said niacin, at least one hydroxy alkyl amide carrier.

24. A method according to claim 23, wherein said composition further comprises an analgesic.

* * * * *